United States Patent
Endo et al.

(10) Patent No.: US 7,022,779 B2
(45) Date of Patent: Apr. 4, 2006

(54) ONE-PACK MOISTURE-CURING EPOXY RESIN COMPOSITION

(75) Inventors: Takeshi Endo, Yamagata (JP); Fumio Sanda, Kyoto (JP); Hisakazu Horii, Osaka (JP); Kentaro Suzuki, Osaka (JP); Nobuki Matsuura, Osaka (JP)

(73) Assignee: Konishi Co., Ltd., Osaka (JP)

( * ) Notice: Subject to any disclaimer, the term of this patent is extended or adjusted under 35 U.S.C. 154(b) by 183 days.

(21) Appl. No.: 10/381,741

(22) PCT Filed: Dec. 17, 2001

(86) PCT No.: PCT/JP01/11072

§ 371 (c)(1),
(2), (4) Date: Apr. 4, 2003

(87) PCT Pub. No.: WO02/50155

PCT Pub. Date: Jun. 27, 2002

(65) Prior Publication Data

US 2004/0019161 A1    Jan. 29, 2004

(30) Foreign Application Priority Data

Dec. 18, 2000  (JP) ............... 2000-383380
Mar. 2, 2001   (JP) ............... 2001-058696

(51) Int. Cl.
C08L 63/00 (2006.01)
C08L 63/02 (2006.01)

(52) U.S. Cl. ............ 525/530; 525/455; 525/502; 525/504; 525/523

(58) Field of Classification Search ......... 525/531, 525/532
See application file for complete search history.

(56) References Cited

U.S. PATENT DOCUMENTS

| | | | | |
|---|---|---|---|---|
| 5,198,524 A | * | 3/1993 | Bush et al. | 528/87 |
| 5,889,124 A | * | 3/1999 | Ando et al. | 525/403 |
| 6,045,873 A | | 4/2000 | Adachi et al. | 427/410 |
| 6,525,159 B1 | * | 2/2003 | Okuhira et al. | 528/26 |

FOREIGN PATENT DOCUMENTS

| EP | 552795 A1 | * | 7/1993 |
|---|---|---|---|
| EP | 0 890 594 A1 | | 1/1999 |
| FR | 1577305 | * | 8/1969 |
| JP | 63273629 A | * | 11/1988 |
| JP | 03192183 A | * | 8/1991 |
| JP | 4-1220 | | 1/1992 |
| JP | 05009267 A | * | 1/1993 |
| JP | 07-188634 | | 7/1995 |
| JP | 08-157563 | | 6/1996 |
| JP | 8-217859 | | 8/1996 |
| JP | 09328668 A | * | 12/1997 |
| JP | 11-021532 | | 1/1999 |
| JP | 11302327 A | * | 11/1999 |
| JP | 11-349663 | | 12/1999 |
| JP | 2000-044773 | | 2/2000 |
| JP | 2000044914 A | * | 2/2000 |
| WO | WO98/31722 A1 | | 7/1998 |

OTHER PUBLICATIONS

Chemical abstracts registry No. 4986-89-4 for pentaerythritol tetraacrylate, 1967.*
Chemical abstracts registry No. 15625-89-5 for trimethylolpropane triacrylate, 1967.*

* cited by examiner

Primary Examiner—Robert Sellers
(74) Attorney, Agent, or Firm—Westerman, Hattori, Daniels & Adrian, LLP

(57) ABSTRACT

A one-pack moisture-curing epoxy resin composition which can be cured at ordinary temperatures and is improved in storage stability without impairing the quickness of curing, i.e., is excellent in two properties incompatible with each other. This composition includes one ore more members selected from the group consisting of vinyl carboxylates of the general formula (1) and epoxy-containing silyl compounds of the general formula (2), one or more members selected from the group consisting of ketimines and oxazolidines, and an epoxy resin. (1) [In the general formula (1), $R_1$, $R_2$, $R_3$, and $R_4$ are each independently hydrogen or an organic group; and n is an integer of 1 or above] (2) [In the general formula (2), $R_5$ and $R_6$ are each independently alkyl; $R_7$ is an epoxy-containing organic group; and n is an integer of 1 to 3]

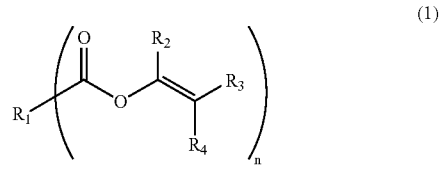

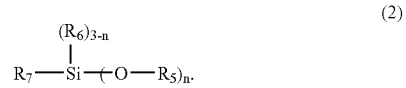

1 Claim, No Drawings

ONE-PACK MOISTURE-CURING EPOXY RESIN COMPOSITION

TECHNICAL FIELD

The present invention relates to a one-pack moisture curable epoxy resin composition having excellent curing properties and good storage stability. Particularly, the present invention relates to a one-pack moisture curable epoxy resin composition having excellent curing properties and good storage stability and suitable as a one-pack room-temperature curable epoxy adhesive, one-pack room-temperature curable epoxy putty material, one-pack room-temperature curable epoxy paint, one-pack room-temperature curable epoxy coating material and one-pack room-temperature curable epoxy potting material.

BACKGROUND ART

An epoxy resin composition is excellent in physical strength and adhesion and has been widely used as an adhesive, putty material, paint and coating material. Since the conventional epoxy resin composition uses a highly reactive amine compound as a hardener, it is a two-pack type characterized in that an epoxy resin and the hardener component are mixed together right before use of the two-pack type. However, since the two-pack epoxy resin composition requires such operations as measuring and mixing, it has poor workability. Further, due to complication of the operations, the two-pack epoxy resin composition also has problems such as a measuring error and inadequate mixing. In addition, the two-pack epoxy resin composition also has a problem that time in which it can be used is limited since a chemical reaction in the two-pack type is initiated by mixing.

Under the circumstances, a variety of studies on a one-pack epoxy resin composition have been made, and a number of techniques for a one-pack epoxy resin composition using a moisture hydrolyzable latent hardener, notably a ketimine compound and an oxazolidine compound, are known. In particular, from an industrial standpoint, a variety of techniques for a one-pack epoxy resin composition using a ketimine compound obtained from methyl isobutyl ketone as a carbonyl compound have been disclosed.

The ketimine compound and the oxazolidine compound are well-known as a latent hardener for an epoxy resin and an isocyanate-terminated urethane polymer. Hereinafter, a reaction mechanism of a composition comprising the ketimine compound or oxazolidine compound as a latent hardener and an epoxy resin will be described. Firstly, as a first reaction, the ketimine compound reacts with moisture in the air and is hydrolyzed so as to produce a primary amine compound having active hydrogen. The oxazolidine compound reacts with moisture in the air so as to produce a secondary amino alcohol. Thus, the first reaction is a process in which the latent hardener is hydrolyzed by moisture. Subsequently, as a second reaction, the produced amine compound having active hydrogen reacts with the epoxy resin, and by this mechanism, the epoxy resin composition is cured. Hence, the second reaction is a process in which the hydrolyzed latent hardener chemically reacts with the epoxy resin. That is, the reaction mechanism of the composition comprising the latent hardener and the epoxy resin is a two-step reaction comprising the reaction of the latent hardener with moisture and the reaction of the amine compound with the epoxy resin. In these two processes, the most important points with respect to the compositions comprising these latent hardeners and the epoxy resin are that (1) the quicker the hydrolysis of the latent hardener such as the ketimine compound proceeds, quicker-curability can be obtained and that (2) the higher the reactivity of the amine compound resulting from the hydrolysis, the more easily physical properties such as quick curability and high strength are obtained. However, when a ketimine compound which is hydrolyzed quickly is used, the ketimine compound is liable to be hydrolyzed during production or storage of the one-pack epoxy resin, so that it becomes difficult to obtain good storage stability. Hence, it was the limitation of the prior art that it could not help but relying on means using a ketimine compound obtained from an amine compound having high reactivity with the epoxy resin and having low hydrolyzability, in consideration of storage stability. Thus, since there is a dilemma that an improvement in quick curability causes impairment of storage stability, a technique of achieving practical quick curability and practical storage stability simultaneously in the composition comprising the ketimine compound and the epoxy resin is not yet found at all.

Meanwhile, recently, a technique of improving storage stability by use of a specific ketimine compound obtained from a carbonyl compound having steric hindrance is disclosed in WO98/31722. The specific ketimine compound has low hydrolyzability since water hardly makes contact with a site showing hydrolyzability due to its steric structure. Therefore, the ketimine compound has the conventional problem that although it can impart good storage stability, it fails to impart good curing properties such as quick curability. That is, when the specific ketimine compound is used, there arises a problem that curing of an epoxy resin composition proceeds slowly, so that initial adhesive strength and mechanical strength are slow to become in effect. It takes long-time curing to attain practicable physical properties, so that the ketimine compound is practically unsatisfactory. Consequently, even this technique is not a technique capable of achieving practical curing properties and practical storage stability simultaneously. That is, it is a technical means which is an extension of the prior art.

Thus, if a composition having excellent storage stability and excellent curing properties is found out of compositions comprising a ketimine compound or oxazolidine compound as a latent hardener and an epoxy resin, it becomes a fundamental technique for an adhesive, putty material, paint, coating material and potting material using them, so that usefulness of such a composition in industry is significantly improved.

Under the circumstances, an object of the present invention is to provide a one-pack moisture curable epoxy resin composition which can be cured at room temperature, shows balanced contradictory properties, i.e., has significantly excellent storage stability without impairing curability, and also has excellent deep curability.

DISCLOSURE OF THE INVENTION

The present inventors have made intensive studies so as to achieve the above object. As a result, they have found that a one-pack moisture curable epoxy resin composition comprising a vinyl carboxylate compound or a silane compound having an epoxy group and a ketimine compound or an oxazolidine compound shows significantly excellent storage stability. They have also found that when a vinyl carboxylate compound or a silyl compound having an epoxy group is added to a one-pack moisture curable epoxy resin composition containing a ketimine compound or oxazolidine compound which is hydrolyzed by moisture in the air so as to produce an amine compound, storage stability can be further improved without impairing curing properties such as rises of adhesive property and mechanical strength. Further, they have found that an epoxy resin composition containing a silyl compound having an epoxy group has exceptionally excellent deep curability. It has been confirmed that the technique is a function of not inhibiting having but achieving the above practical curing properties and storage stability simultaneously. More specifically, although there has been a dilemma in the prior art that storage stability must be improved at the sacrifice of curing properties, the above technique has been confirmed to be a technique for eliminating the dilemma.

That is, the invention of the present application is based on an effect that the epoxy-group-containing silyl compound added to the above epoxy resin composition removes water entering the composition during its production or storage in a container before the ketimine compound or oxazolidine compound reacts with the water so as to allow the ketimine compound or oxazolidine compound to exist stably and an effect that the epoxy group reacts with the amine compound so as to improve storage stability without impairing physical properties of a cured product. Further, the invention of the present application is also based on an effect that the vinyl carboxylate compound added to the above epoxy resin composition blocks active hydrogen of the amine compound resulting from hydrolysis of the ketimine compound or oxazolidine compound during storage of the composition in a container so as to further improve storage stability. These two techniques are techniques for achieving the desired object of having practical curing properties and excellent storage stability. The techniques act on the different reactions constituting the two-step reaction of the ketimine compound or oxazolidine compound with the epoxy resin, and each of the techniques is still effective alone in improving storage stability. Further, since the techniques exhibit their effects of improving storage stability in the different reactions steps without offsetting the effects, storage stability is further improved by using these two techniques simultaneously.

Based on these findings, the present inventors have widely studied types of compounds having such properties, amounts of these compounds to be mixed with the epoxy resin, and techniques of synthesizing these compounds. As a result, they have succeeded in development of a one-pack moisture curable epoxy resin composition which can be used without any problems even after long-time storage without impairing the speeds of rises of initial adhesive strength, adhesive strength and mechanical strength and have completed the present invention.

As means of the present invention for achieving the above object, a first invention is a one-pack moisture curable epoxy resin composition comprising:

one or two or more compounds selected from the group consisting of a vinyl carboxylate compound represented by the following chemical formula (1) and a silyl compound represented by the following chemical formula (2) which has an epoxy group in an organic group, one or two or more compounds selected from the group consisting of a ketimine compound represented by the following chemical formula (4) which is obtained by reaction of a carbonyl compound represented by the following chemical formula (3) with an amine compound having a primary amino group and an oxazolidine compound represented by the following chemical formula (5) which is obtained by dehydration condensation of a carbonyl compound and an aminoalcohol compound, and an epoxy resin:

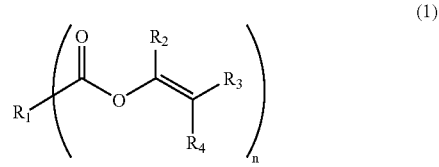

wherein $R_1$, $R_2$, $R_3$ and $R_4$ are each a hydrogen atom or an organic group and they may be the same or different, and n is an integer of 1 or more,

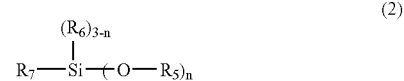

wherein $R_5$ and $R_6$ are each an alkyl group and they may be the same or different,
$R_7$ is an organic group having an epoxy group,
n is an integer of 1 to 3,

wherein $R_8$ and $R_9$ are each an alkyl group and they may be the same or different,

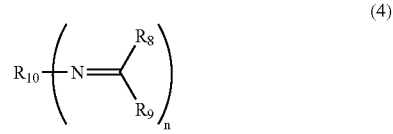

wherein $R_{10}$ is a residue excluding a primary amino group of an amine compound,
$R_8$ and $R_9$ are each an alkyl group and they may be the same or different, and
n is an integer of 1 or more, and

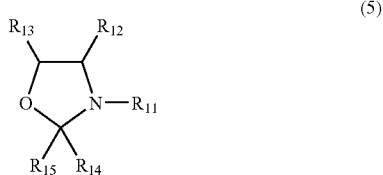

wherein $R_{11}$, $R_{12}$, $R_{13}$, $R_{14}$ and $R_{15}$ are each a hydrogen atom or an organic group.

A silyl compound having an epoxy group in the present invention is a compound represented by the above chemical formula (2) which has a hydrolyzable alkoxysilyl group comprising an Si—O bond and an epoxy group. The alkoxysilyl site causes a dealcoholization reaction with water, thereby consuming the water. The silyl compound reacts with and consumes a small amount of water entering the composition system during storage before the ketimine compound reacts with the water so as to prevent hydrolysis of the ketimine compound. Since it is prevented that the ketimine compound is hydrolyzed during storage and produces an amine compound, storage stability is improved. The silyl compound also reacts with water quickly upon use of the adhesive composition. In that case, however, since a large amount of water enters the system, the ketimine compound represented by the above chemical formula (4) in the present invention also reacts with water quickly due to its high hydrolyzability. That is, this implies that the composition of the present invention does not require long-time curing so as to obtain practicable physical properties.

Further, in such a silyl compound, the epoxy group also acts as a reactive site in addition to the hydrolyzable Si—O bond. Hence, it has more crosslinkable sites in a molecule. Accordingly, a more complicated crosslinked structure is formed more quickly, and curing occurs in a deeper portion even after curing over a predetermined time period. That is, this implies that it has excellent deep curability. The technique is a function of not inhibiting having but achieving the above practical curing properties and storage stability simultaneously.

A vinyl carboxylate compound used in the present invention is a compound represented by the above chemical formula (1) which has a C=C—O—C=O bond. The site reacts with an amine compound so as to produce an amide compound. The vinyl carboxylate compound reacts with a small amount of amine compound resulting from hydrolysis of the ketimine compound or oxazolidine compound by a small amount of water entering the composition system during storage so as to produce an amide compound having low activity with the epoxy resin, thereby improving storage stability. The vinyl carboxylate compound also reacts with the amine compound upon use of the adhesive composition. However, since its amount is small whereas the amount of the amine compound resulting from the hydrolysis is large, it has no influence on curing properties. That is, this implies that storage stability can be improved without impairing curing properties upon use.

By incorporating the above vinyl carboxylate compound into the one-pack epoxy resin composition, storage stability could be improved dramatically.

A ketimine compound used in the present invention is a compound represented by the above chemical formula (4) which has a hydrolyzable C=N double bond. The site reacts with water so as to be hydrolyzed into an amine compound having a primary amino group and a carbonyl compound having two same or different alkyl groups. In the one-pack moisture curable epoxy resin composition, the produced amine compound reacts with the epoxy resin so as to cure the composition.

An oxazolidine compound used in the present invention is a hydrolyzable cyclic compound represented by the above chemical formula (5) which has an O atom and an N atom on the same carbon. The site reacts with water so as to be hydrolyzed into a secondary aminoalcohol and a carbonyl compound having two same or different alkyl groups. In the one-pack moisture curable epoxy resin composition, the produced amine compound reacts with the epoxy resin so as to cure the composition.

A second invention is a one-pack moisture curable epoxy resin composition comprising:
a vinyl carboxylate compound represented by the above chemical formula (1),
one or two or more compounds selected from the group consisting of a ketimine compound represented by the above chemical formula (4) which is obtained by reaction of a carbonyl compound represented by the above chemical formula (3) with an amine compound having a primary amino group and an oxazolidine compound represented by the above chemical formula (5) which is obtained by dehydration condensation of a carbonyl compound and an aminoalcohol compound, and an epoxy resin.

A third invention is a one-pack moisture curable epoxy resin composition comprising a silyl compound represented by the above chemical formula (2) which has an epoxy group in an organic group, a ketimine compound represented by the above chemical formula (4), and an epoxy resin.

A fourth invention is a one-pack moisture curable epoxy resin composition comprising:
a vinyl carboxylate compound represented by the above chemical formula (1),
one or two or more compounds selected from the group consisting of a silyl compound represented by the following chemical formula (6) and a silyl compound represented by the following chemical formula (7),
a ketimine compound represented by the above chemical formula (4) which is obtained by reaction of a carbonyl compound represented by the above chemical formula (3) with an amine compound having a primary amino group, and an epoxy resin:

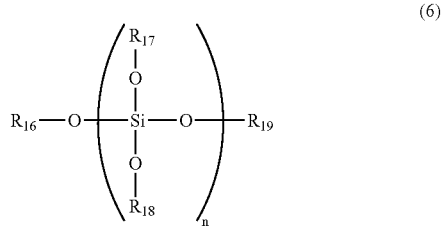

(6)

wherein $R_{16}$, $R_{17}$, $R_{18}$ and $R_{19}$ are each an alkyl group and they may be the same or different, and
n is an integer of 1 or more, and

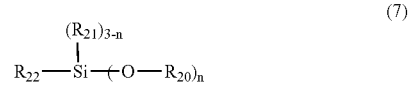

(7)

wherein $R_{20}$ and $R_{21}$ are each an alkyl group and they may be the same or different,
$R_{22}$ is an organic group, and
n is an integer of 1 to 3.

Since these silyl compounds have hydrolyzable alkoxysilyl groups, they can suppress reaction of the ketimine compound or oxazolidine compound with water entering at the time of production or during storage. That is, the composition of the present invention is a one-pack moisture curable epoxy resin composition which does not require long-time curing so as to exhibit satisfactory strength.

BEST MODE FOR CARRYING OUT THE INVENTION

Hereinafter, an embodiment of the present invention will be described in detail.

A vinyl carboxylate compound used in the present invention may be any compound represented by the following chemical formula (1) which has a vinyl carboxylate group. Specific examples of the compound represented by the following chemical formula (1) include vinyl acetate, vinyl butyrate, vinyl caproate, vinyl caprylate, vinyl caprate, vinyl laurate, vinyl myristate, vinyl palmitate, vinyl stearate, vinyl cyclohexane carboxylate, vinyl octoate, vinyl monochloroacetate, divinyl adipate, vinyl methacrylate, vinyl crotonate, vinyl sorbate, vinyl benzoate, and vinyl cinnamate. It is needless to say that the vinyl carboxylate used in the present invention is not limited to these vinyl carboxylates and two or more vinyl carboxylates may be used in combination.

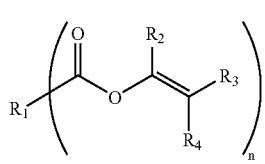

(1)

wherein $R_1$, $R_2$, $R_3$ and $R_4$ are each a hydrogen atom or an organic group and they may be the same or different, and n is an integer of 1 or more.

These vinyl carboxylates have high reactivity with an amine compound. Therefore, an amine compound resulting from hydrolysis by water entering during storage reacts with the vinyl carboxylate before reacting with an epoxy resin so as to prevent an increase in viscosity which is a problem in terms of quality.

A silyl compound used in the present invention and having an epoxy group in an organic group may be any compound represented by the following chemical formula (2) which has an epoxy group and an alkoxysilyl group in a molecule. Specific examples thereof include γ-glycidoxypropyltrimethoxysilane represented by the following chemical formula (8) and γ-glycidoxypropyltriethoxysilane represented by the following chemical formula (9). Commercial products thereof are exemplified by KBM403 and KBE403 (products of SHIN-ETSU CHEMICAL CO., LTD.), respectively, but are not limited to them. It is needless to say that compounds represented by the following chemical formula (2) may be used in combination of two or more and may also be used in combination with a silyl compound represented by the above chemical formula (6) or (7):

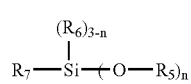

(2)

wherein $R_5$ and $R_6$ are each an alkyl group and they may be the same or different,
$R_7$ is an organic group having an epoxy group, and
n is an integer of 1 to 3, and

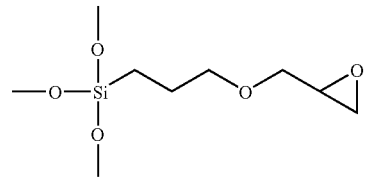

(8)

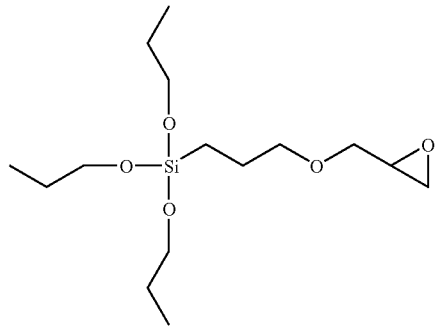

(9)

A ketimine compound used in the present invention is a hydrolyzable compound represented by the following chemical formula (4) which has a double bond between a carbon atom and a nitrogen atom. The ketimine compound is a compound obtained by reaction of a carbonyl compound in which same or different alkyl groups are bonded to a carbon atom in a carbonyl group with an amine compound having a primary amino group. The ketimine compound may be any compound having a structure represented by the chemical formula (4). Specific examples thereof include N,N'-di(1,3-dimethylbutylidene)-1,3-bisaminomethylcyclohexane represented by the following chemical formula (10) and N,N'-di(1,3-dimethylbutylidene)-meta-xylylene diamine represented by the following chemical formula (11). These are a dehydration condensate of 1,3-bisaminomethylcyclohexane and methyl isobutyl ketone and a dehydration condensate of meta-xylylene diamine and methyl isobutyl ketone, respectively.

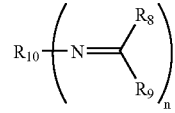

(4)

wherein $R_{10}$ is a residue excluding a primary amino group of an amine compound,
$R_8$ and $R_9$ are each selected from the group consisting of alkyl groups and they may be the same or different, and
n is an integer of 1 or more, and

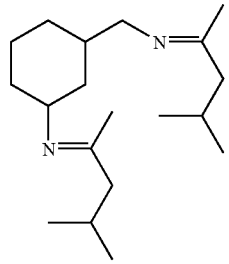

(10)

-continued

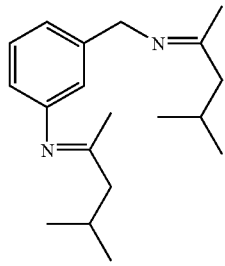
(11)

A carbonyl compound which is used as a raw material of the ketimine compound used in the present invention may be any carbonyl compound represented by the following chemical formula (3) in which same or different alkyl groups are bonded to a carbon atom in a carbonyl group. Specific examples thereof include acetone, methyl ethyl ketone, methyl isobutyl ketone, methyl isopropyl ketone, and methyl isopentyl ketone.

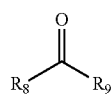
(3)

wherein $R_8$ and $R_9$ are each an alkyl group and they may be the same or different.

An amine compound which is used as a raw material of the ketimine compound used in the present invention may be any compound having a primary amino group. Specific examples thereof include, but not limited to, ethylene diamine, diethylene triamine, 1,3-bisaminomethylcyclohexane, norbornane diamine, meta-xylylene diamine, isophorone diamine, bis(4-aminocyclohexyl)methane, a polyamine having a polyoxylene skeleton, N-β(aminoethyl)γ-aminopropyltrimethoxysilane, N-β(aminoethyl)γ-aminopropylmethyldimethoxysilane, γ-aminopropyltrimethoxysilane, and γ-aminopropyltriethoxysilane. An amine compound having two or more primary amino groups in a molecule is preferred since excellent mechanical strength is obtained.

The ketimine compound may be produced by any production method. For example, it can be produced by mixing the above carbonyl compound with the above amine compound in the absence of a solvent or in the presence of a nonpolar solvent (such as hexane, cyclohexane, toluene or benzene), subjecting the mixture to reflux under heating, and removing produced water by azeotropy. As the carbonyl compound and amine compound used as raw materials, one or two or more compounds selected from the group consisting of a variety of carbonyl compounds and one or two or more compounds selected from the group consisting of a variety of amine compounds may be used.

A specific oxazolidine compound used in the present invention is a hydrolyzable compound represented by the following chemical formula (5) which has an N atom and an O atom on the same carbon. The oxazolidine compound is a compound obtained by reaction of a carbonyl compound having same or different alkyl groups bonded to a C atom in a carbonyl group with a secondary aminoalcohol compound. The specific oxazolidine compound may be any compound having a structure represented by the chemical formula (5):

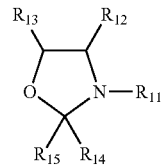
(5)

wherein $R_{11}$, $R_{12}$, $R_{13}$, $R_{14}$ and $R_{15}$ are each a hydrogen atom or an organic group.

The carbonyl compound which is used as a raw material of the oxazolidine compound used in the present invention may be any carbonyl compound represented by the following chemical formula (3) which has same or different alkyl groups bonded to a carbon atom in a carbonyl group. Specific examples of such a carbonyl compound include acetone, methyl ethyl ketone, methyl isobutyl ketone, methyl isopropyl ketone, methyl isopentyl ketone, diethyl ketone, dipropyl ketone, dibutyl ketone, ethyl propyl ketone, and ethyl butyl ketone.

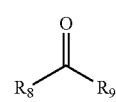
(3)

wherein $R_8$ and $R_9$ are each an alkyl group and they may be the same or different.

The aminoalcohol which is used as a raw material of the oxazolidine compound used in the present invention may be any compound having a secondary ethanolamine structure. Specific examples thereof include, but not limited to, N-methylethanolamine, N-ethylethanolamine, N-propylethanolamine, N-ethyl-2-methylethanolamine, and diethanolamine. Of these, N-methylethanolamine and N-ethylethanolamine are preferred since they have high reactivity with an epoxy resin.

The oxazolidine compound may be produced by any production method. For example, it can be produced by mixing the above carbonyl compound with the above aminoalcohol compound in the absence of a solvent or in the presence of a nonpolar solvent (such as hexane, cyclohexane, toluene or benzene), subjecting the mixture to reflux under heating, and removing produced water by azeotropy. As the carbonyl compound and aminoalcohol compound used as raw materials, one or two or more compounds selected from the group consisting of a variety of carbonyl compounds and one or two or more compounds selected from the group consisting of a variety of aminoalcohol compounds may be used.

Further, it is needless to say that two or more of the above ketimine compounds and the above oxazolidine compounds may be used in the one-pack epoxy resin composition. In addition, as long as curing properties and storage stability are not impaired, other latent hardeners may also be used.

The epoxy resin may be any epoxy resin having an epoxy group which is capable of reacting with the amine compound resulting from hydrolysis of the ketimine compound or oxazolidine compound at the time of its use. Illustrative examples of the epoxy resin include a biphenyl epoxy resin, a bisphenol-A epoxy resin, a bisphenol-F epoxy resin, a bisphenol-AD epoxy resin and a bisphenol-S epoxy resin which are obtained by reacting biphenyl, bisphenol A, bisphenol F, bisphenol AD and bisphenol S with epichlorhydrin, epoxy resins resulting from hydrogenation or bromination of these epoxy resins, a glycidyl ester epoxy resin, a novolac epoxy resin, an urethane-modified epoxy resin having an urethane bond, a nitrogen-containing epoxy resin resulting from epoxidation of meta-xylene diamine or hydantoin, and a rubber-modified epoxy resin containing a polybutadiene or NBR. The epoxy resin is not limited to these epoxy resins, and two or more epoxy resins may be used in combination.

The silyl compound used in the present invention may be any compound represented by the following chemical formula (6) or (7) which has an alkoxysilyl group. Specific examples of the compound represented by the following chemical formula (6) include monomers such as tetramethoxysilane, tetraethoxysilane and tetrabutoxysilane, and polymers thereof. Specific examples of the compound represented by the following chemical formula (7) include silane coupling agents having organic groups such as an alkyl group, a vinyl group, an epoxy group, an isocyanate group and a ketimine group. Specific examples of the silane coupling agents include dimethyldimethoxysilane, methyltrimethoxysilane, methyltriethoxysilane, vinyltrimethoxysilane, vinyltriethoxysilane, γ-glycidoxypropyltrimethoxysilane, γ-glycidoxypropyltriethoxysilane, γ-glycidoxypropylmethyldiethoxysilane, and γ-isocyanatepropyltriethoxysilane. It is needless to say that the silane coupling agents are not limited to those enumerated above and two or more silane coupling agents may be used in combination.

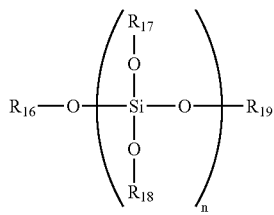

(6)

wherein $R_{16}$, $R_{17}$, $R_{18}$ and $R_{19}$ are each an alkyl group and they may be the same or different, and
n is an integer of 1 or more, and

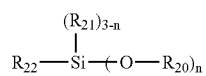

(7)

wherein $R_{20}$ and $R_{21}$ are each an alkyl group and they may be the same or different,
$R_{22}$ is an organic group, and
n is an integer of 1 to 3.

As for the amount of the vinyl carboxylate based on the epoxy resin in the present invention, it is preferably 1 to 30 mol % per mol of an epoxy group. When the amount is larger than the above range, the vinyl carboxylate hinders reaction with the epoxy resin by reacting with the amine compound produced from the ketimine compound or oxazolidine compound. When the amount is smaller than the above range, the vinyl carboxylate cannot fully react with the amine compound resulting from hydrolysis of the ketimine compound or oxazolidine compound by a small amount of water entering the composition during storage, so that storage stability cannot be improved. The amount preferably falls within the above range since practical storage stability can be obtained. The amount is more preferably 5 to 15 mol % since more ideal storage stability can be obtained.

As for the amount of the silyl compound represented by the above chemical formula (2), (6) or (7) based on the epoxy resin used in the present invention, it varies according to the type of silyl compound to be used. However, it is preferred that the amount of the silyl compound be not smaller than 10 parts by weight based on 100 parts by weight of the epoxy resin. When the amount is lower than the above range, the amount of the silyl compound is too small to fully consume a small amount of water entering the composition system during storage and to suppress hydrolysis of the ketimine compound or oxazolidine compound, so that practical storage stability cannot be obtained. The amount preferably falls within the above range since practical storage stability can be obtained. The amount is more preferably not smaller than 30 parts by weight since the most superior storage stability can be obtained.

The mixing ratio of the ketimine compound and the epoxy compound in the present invention is determined according to the equivalent of active hydrogen in the amine compound resulting from hydrolysis of the ketimine compound and the equivalent of an epoxy group in the epoxy compound. That is, the equivalent of the active hydrogen in the amine compound resulting from the hydrolysis of the ketimine compound is preferably 0.5 to 2.0 times as much as the equivalent of the epoxy group. When the mixing ratio is lower than the above range, the epoxy group becomes excessive, crosslinking in a cured product does not proceed satisfactorily, and practical mechanical strength cannot be obtained. When the mixing ratio is higher than the above range, the amine compound resulting from the hydrolysis becomes excessive, that is, the active hydrogen becomes excessive, and in this case as well, due to the same reason, practical mechanical strength cannot be obtained. The mixing ratio preferably falls within the above range since a crosslinked structure with practical mechanical strength can be obtained. The mixing ratio is more preferably 0.8 to 1.2 times since an ideal crosslinked structure with better mechanical strength as an adhesive composition can be obtained.

As for the amount of the oxazolidine compound based on the epoxy compound in the present invention, it is preferably 10 to 40 parts by weight based on 100 parts by weight of the epoxy resin having a weight per epoxide of 190. When the amount is lower than the above range, the epoxy group becomes excessive, crosslinking in a cured product does not proceed satisfactorily, and practical mechanical strength cannot be obtained. When the amount is higher than the above range, the amine compound resulting from hydrolysis becomes excessive, that is, active hydrogen becomes excessive, and in this case as well, due to the same reason, practical mechanical strength cannot be obtained. The amount preferably falls within the above range since a crosslinked structure with practical mechanical strength can be obtained. The amount is more preferably 20 to 30 parts by weight since an ideal crosslinked structure with better mechanical strength as an adhesive composition can be obtained.

In addition to the foregoing compounds, the composition of the present invention may also contain a filler such as calcium carbonate or titanium oxide, a coupling agent such as epoxysilane or vinylsilane, a plasticizer, a thixotropy imparting agent, a pigment, a dye, an age resistor, an antioxidant, an antistatic agent, a flame retardant, an adhesion imparting agent, a dispersant, a solvent and the like in such an amount that does not impair the effect of the present invention. In this case, it gives a favorable result on storage stability that the influence of water in the above components which may be contained is removed as much as possible.

A production method of the composition of the present invention is not particularly limited but is preferably produced by fully kneading its raw materials under a nitrogen atmosphere or a reduced pressure by use of a stirrer such as a mixer. An example of the production method is as follows. An epoxy resin is put in a closed processing furnace equipped with a stirrer, a condenser, a heater, a low-pressure dehydrator and a nitrogen current ventilator. Using the nitrogen current ventilator, a modifier or an additive is added to the epoxy resin as desired and they are mixed uniformly under nitrogen reflux. Thereafter, one or two or more compounds selected from the group consisting of a ketimine compound and an oxazolidine compound are added eventually and mixed uniformly so as to obtain a one-pack moisture curable adhesive composition. Then, the one-pack moisture curable adhesive composition is put in a nitrogen-substituted closed container so as to become a final product. When water is contained in the modifier or additive, the composition is liable to be cured and storage stability is liable to deteriorate during storage. Hence, it is preferable to remove the water from the modifier or additive in advance. The water may be removed before addition of the modifier or additive or removed by means of heating or decompression after they are added to the epoxy resin.

EXAMPLES

Hereinafter, the present invention will be described based on Examples. The present invention, however, shall not be limited to the Examples.

[Synthesis of Ketimine Compound]

Synthesis Example 1

142 g of 1,3-bisaminomethylcyclohexane (product of Mitsubishi Gas Chemical Company Inc., trade name: 1,3-BAC) and 300 g of methyl isobutyl ketone corresponding to 3 time mole equivalents were put in a flask and, while produced water was removed by azeotropy, they were allowed to react for 20 hours at temperatures (120 to 150° C.) at which toluene and methyl isobutyl ketone were refluxed. Then, excessive methyl isobutyl ketone and toluene were distilled out so as to obtain a ketimine compound A.

Synthesis Example 2

A ketimine compound B was obtained in the same manner as in Synthesis Example 1 except that 154 g of norbornane diamine (product of Mitsui Chemicals, Inc., trade name: NBDA) was used as an amine compound.

Example 1

100 parts by weight of epoxy resin (product of YUKA SHELL EPOXY CO., LTD. (corporate name change: Japan Epoxy Resins), trade name: Epikote 828), 40 parts by weight of heavy calcium carbonate (product of NITTO FUNKA KOGYO CO., LTD., trade name: NS100) and 80 parts by weight of surface-treated calcium carbonate (product of MARUO CALCIUM CO., LTD., trade name: MS700) were heated at 100° C. under a reduced pressure of 15 Torr for 2 hours and stirred and mixed until the mixture became uniform. After the mixture became uniform, it was cooled to room temperature. Then, to the mixture, 30 parts by weight of an oxazolidine compound (product of San-Apro Ltd., trade name: MS-PLUS) as a hardener for the epoxy resin and 6.6 parts by weight of vinyl butyrate as a stabilizer were added, and the resulting mixture was stirred under a reduced pressure so as to obtain a one-pack moisture curable epoxy resin composition.

Example 2

A one-pack moisture curable epoxy resin composition was obtained in the same manner as in Example 1 except that 40 parts by weight of epoxy silane coupling agent (product of SHIN-ETSU CHEMICAL CO., LTD., trade name: KBM403) was used in place of vinyl butyrate as a stabilizer.

Example 3

A one-pack moisture curable epoxy resin composition was obtained in the same manner as in Example 1 except that 45 parts by weight of the ketimine compound A was used in place of the oxazolidine compound as a latent hardener.

Example 4

A one-pack moisture curable epoxy resin composition was obtained in the same manner as in Example 2 except that 45 parts by weight of the ketimine compound A was used in place of the oxazolidine compound as a latent hardener.

Example 5

A one-pack moisture curable epoxy resin composition was obtained in the same manner as in Example 4 except that 6.6 parts by weight of vinyl butyrate was added as a stabilizer.

Example 6

A one-pack moisture curable epoxy resin composition was obtained in the same manner as in Example 5 except that the ketimine compound B was used in place of the ketimine compound A as a latent hardener.

Example 7

A one-pack moisture curable epoxy resin composition was obtained in the same manner as in Example 5 except that 10 parts by weight of oxazolidine compound as a latent hardener was added in place of reducing the amount of the ketimine compound A as a latent hardener to 30 parts by weight.

Example 8

A one-pack moisture curable epoxy resin composition was obtained in the same manner as in Example 3 except that 40 parts by weight of ethyl silicate (Toshiba Silicones Co., Ltd., trade name: TSL8124) was added as a stabilizer.

Example 9

A one-pack moisture curable epoxy resin composition was obtained in the same manner as in Example 8 except that 13.1 parts by weight of vinyl laurate was used in place of vinyl butyrate as a stabilizer.

Comparative Example 1

A one-pack moisture curable epoxy resin composition was obtained in the same manner as in Example 1 except that vinyl butyrate was not used.

Comparative Example 2

A one-pack moisture curable epoxy resin composition was obtained in the same manner as in Example 3 except that vinyl butyrate was not used.

The following tests were conducted by use of the one-pack moisture curable epoxy resin compositions of Examples 1 to 9 and Comparative Examples 1 and 2. The results of Examples 1 to 9 and Comparative Examples 1 and 2 are shown in Tables 1 and 2.

TABLE 1

| | | Ex.1 | Ex.2 | Ex.3 | Ex.4 | Ex.5 | Ex.6 |
|---|---|---|---|---|---|---|---|
| Epoxy Resin | Epikote 828 | 100 | 100 | 100 | 100 | 100 | 100 |
| Heavy Calcium Carbonate | NS100 | 40 | 40 | 40 | 40 | 40 | 40 |
| Treated Calcium Carbonate | MS700 | 80 | 80 | 80 | 80 | 80 | 80 |
| Oxazolidine Compound | MS-PLUS | 30 | 30 | | | | |
| Ketimine Compound A | 1,3-BAC-MIBK | | | 45 | 45 | 45 | |
| Ketimine Compound B | NBDA-MIBK | | | | | | 45 |
| Vinyl Ester Compound A | Vinyl Butyrate | 6.6 | | 6.6 | | 6.6 | 6.6 |
| Vinyl Ester Compound B | Vinyl Laurate | | | | | | |
| Ethyl Silicate | TSL8124 | | | | | | |
| Epoxysilane Compound | KBM403 | | 40 | | 40 | 40 | 40 |
| Adhesive Property (Mortar Bending Adhesive Strength) upper row: N/mm² lower row: condition of failure | 23° C., after 7 days | 5.8 Cohesive Failure | 5.6 Cohesive Failure | 7.5 Cohesive Failure Partial Mortar Failure | 7.9 Mortar Failure | 9.2 Mortar Failure | 8.9 Mortar Failure |
| Deep Curability | 23° C., after 7 days | Good | Excellent | Acceptable | Good | Good | Good |
| Stability | 20° C., after 2 months | Excellent | Excellent | Excellent | Excellent | Excellent | Excellent |
| | 20° C., after 4 months | Excellent | Excellent | Good | Good | Excellent | Excellent |
| | 20° C., after 6 months | Acceptable | Acceptable | Acceptable | Acceptable | Excellent | Excellent |

Ex.: Example

An adhesive property was measured in a mortar bending adhesive test (refer to JIS A6024 Adhesive Property) under various curing conditions.

Deep Curability was measured by charging the composition into a deep container without trapping air therein, allowing the composition to cure at 23° C. for 1 week, and measuring the thickness of a cured product layer excluding the uncured composition.

Stability was measured by placing a sample in a closed cartridge and measuring its viscosity when the sample was stored at various temperature conditions.

TABLE 2

| | | Ex.7 | Ex.8 | Ex.9 | C.Ex.1 | C.Ex.2 |
|---|---|---|---|---|---|---|
| Epoxy Resin | Epikote 828 | 100 | 100 | 100 | 100 | 100 |
| Heavy Calcium Carbonate | NS100 | 40 | 40 | 40 | 40 | 40 |
| Treated Calcium Carbonate | MS700 | 80 | 80 | 80 | 80 | 80 |
| Oxazolidine Compound | MS-PLUS | 10 | | | 30 | |
| Ketimine Compound A | 1,3-BAC-MIBK | 30 | 45 | 45 | | 45 |
| Ketimine Compound B | NBDA-MIBK | | | | | |
| Vinyl Ester Compound A | Vinyl Butyrate | 6.6 | 6.6 | | | |
| Vinyl Ester Compound B | Vinyl Laurate | | | 13.1 | | |
| Ethyl Silicate | TSL8124 | | 40 | 40 | | |
| Epoxysilane Compound | KBM403 | 40 | | | | |
| Adhesive Property (Mortar Bending Adhesive Strength) upper row: N/mm² lower row: condition of failure | 23° C., after 7 days | 8.0 Mortar Failure | 6.5 Cohesive Failure Partial Mortar Failure | 6.1 Cohesive Failure Partial Mortar Failure | 5.5 Cohesive Failure | 6.4 Cohesive Failure Partial Mortar Failure |

TABLE 2-continued

|  |  | Ex.7 | Ex.8 | Ex.9 | C.Ex.1 | C.Ex.2 |
|---|---|---|---|---|---|---|
| Deep Curability Stability | 23° C., after 7 days | Good | Acceptable | Acceptable | Good | Acceptable |
|  | 20° C., after 2 months | Excellent | Excellent | Excellent | Unacceptable | Unacceptable |
|  | 20° C., after 4 months | Excellent | Excellent | Excellent | Unacceptable | Unacceptable |
|  | 20° C., after 6 months | Excellent | Excellent | Excellent | Unacceptable | Unacceptable |

Ex.:Example, C.Ex.: Comparative Example
An adhesive property was measured in a mortar bending adhesive test (refer to JIS A6024 Adhesive Property) under various curing conditions.
Deep Curability was measured by charging the composition into a deep container without trapping air therein, allowing the composition to cure at 23° C. for 1 week, and measuring the thickness of a cured product layer excluding the uncured composition.
Stability was measured by placing a sample in a closed cartridge and measuring its viscosity when the sample was stored at various temperature conditions.

(Adhesive Property)

An adhesive property was measured in accordance with JIS A6024 (refer to adhesive property) of a mortar bending adhesive test under various curing conditions. That is, it was measured in accordance with a standard condition (curing at 23° C. for 7 days) of an adhesive strength test in JIS A6024 (injection epoxy resin for construction repairing). Its unit was $N/mm^2$, and a condition of failure at that time was shown.

(Deep Curability)

The one-pack moisture curable epoxy resin composition was charged into a deep container without trapping air therein and allowed to cure at 23° C. for 1 week. The thickness of a cured product layer excluding the uncured composition was measured. The thickness of the cured product layer was compared and rated on the following four-rank scale of "Excellent", "Good", "Acceptable" and "Unacceptable".
Excellent: 2.0≦Thickness (mm) of cured product after cured at 23° C. for 7 days.
Good: 1.0≦Thickness (mm) of cured product after cured at 23° C. for 7 days<2.0
Acceptable: 0.5≦Thickness (mm) of cured product after cured at 23° C. for 7 days<1.0
Unacceptable: Thickness (mm) of cured product after cured at 23° C. for 7 days<0.5

To rate the characteristic value of the deep curability in the present invention, a characteristic value rated as "Excellent" is the most excellent from a practical standpoint, followed by one rated as "Good". A characteristic value rated as "Acceptable" is inferior to those rated as "Excellent" and "Good" but still has practicability. However, "Unacceptable" represents a characteristic value which is the most inferior and lacks practicability.

(Stability)

Stability was measured by placing a sample in a closed cartridge and measuring its viscosity when stored at various temperature conditions. That is, the one-pack moisture curable epoxy resin composition was filled and sealed in the cartridge and left to stand at 23° C. for various time periods, and then its viscosity was measured. Then, stability was compared with its viscosity immediately after preparation and rated on the following four-rank scale of "Excellent", "Good", "Acceptable" and "Unacceptable". The viscosity was measured at 23° C. by use of a BH-type viscometer at 10 r/min.

Excellent: (viscosity after left to stand)/(viscosity immediately after preparation)≦1.5
Good: 1.5<(viscosity after left to stand)/(viscosity immediately after preparation)≦2
Acceptable: 2<(viscosity after left to stand)/(viscosity immediately after preparation)≦3
Unacceptable: 3<(viscosity after left to stand)/(viscosity immediately after preparation)

To rate the characteristic value of the stability in the present invention, a characteristic value rated as "Excellent" is the most excellent from a practical standpoint, followed by one rated as "Good". A characteristic value rated as "Acceptable" is inferior to those rated as "Excellent" and "Good" but still has practicability. However, "Unacceptable" represents a characteristic value which is the most inferior and lacks practicability.

It is obvious from comparison of Examples 1 and 2 with Comparative Example 1 that the one-pack moisture curable epoxy resin compositions of the Examples show adhesive properties equal to that of the one-pack moisture curable epoxy resin composition of the Comparative Example. Further, it is understood that since the one-pack moisture curable epoxy resin compositions of the Examples show better storage stability than the one-pack moisture curable epoxy resin composition of the Comparative Example, only storage stability is improved without impairing the adhesive properties.

Further, it is obvious from comparison of Examples 3 to 9 with Comparative Example 2 that the one-pack moisture curable epoxy resin compositions of the Examples show adhesive properties which are equal to or better than that of the one-pack moisture curable epoxy resin composition of the Comparative Example. Further, it is understood that since the one-pack moisture curable epoxy resin compositions of the Examples show better storage stability than the one-pack moisture curable epoxy resin composition of the Comparative Example, only storage stability is improved without impairing the adhesive properties. In addition, as is obvious from Example 5 to 7, by concurrent use of the vinyl carboxylate and the epoxysilane as stabilizers, storage stability and inner curability can be improved without impairing curing properties.

POSSIBILITY OF INDUSTRIAL UTILIZATION

As described above, the one-pack moisture curable epoxy resin composition according to the present invention is a room-temperature curable adhesive composition which has balanced contradictory properties, i.e., improving storage stability significantly without impairing quick curability. Accordingly, the one-pack moisture curable epoxy resin composition according to the present invention is suitable for being effectively used in applications in which a conventional two-pack epoxy resin has been used such as an adhesive, putty material, paint, coating material and potting material using the composition.

The invention claimed is:

1. A one-pack moisture curable epoxy resin composition comprising:
   (a) a vinyl carboxylate compound represented by the following chemical formula (1),
   (b) one or two or more compounds selected from the group consisting of a ketimine compound represented by the following chemical formula (4) which is obtained by reaction of a carbonyl compound represented by the following chemical formula (3) with an amine compound having a primary amino group, and an oxazolidine compound represented by the following chemical formula (5) which is obtained by dehydration condensation of a carbonyl compound and an aminoalcohol compound, and
   (c) an epoxy resin:

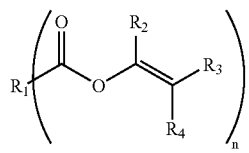

(1)

wherein $R_1$, $R_2$, $R_3$ and $R_4$ are each a hydrogen atom or an organic group and they may be the same or different, and
n is an integer of 1 or more,

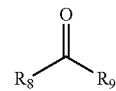

(3)

wherein $R_8$ and $R_9$ are each an alkyl group and they may be the same or different,

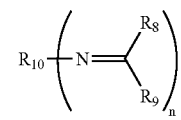

(4)

wherein $R_{10}$ is a residue excluding a primary amino group of an amine compound,
$R_8$ and $R_9$ are each an alkyl group and they may be the same or different, and
n is an integer of 1 or more, and

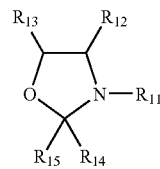

(5)

wherein $R_{11}$, $R_{12}$, $R_{13}$, $R_{14}$ and $R_{15}$ are each a hydrogen atom or an organic group.

* * * * *